United States Patent
Toimela et al.

(10) Patent No.: US 9,381,376 B2
(45) Date of Patent: Jul. 5, 2016

(54) SYSTEMS, DEVICES, AND METHODS FOR QUALITY ASSURANCE OF RADIATION THERAPY

(71) Applicant: Varian Medical Systems International AG, Zug (CH)

(72) Inventors: Lasse Heikki Toimela, Espoo (FI); Janne Nord, Espoo (FI)

(73) Assignee: VARIAN MEDICAL SYSTEMS INTERNATIONAL AG, Zug (CH)

( * ) Notice: Subject to any disclaimer, the term of this patent is extended or adjusted under 35 U.S.C. 154(b) by 78 days.

(21) Appl. No.: 13/650,980

(22) Filed: Oct. 12, 2012

(65) Prior Publication Data
US 2014/0105355 A1    Apr. 17, 2014

(51) Int. Cl.
*A61N 5/00* (2006.01)
*A61N 5/10* (2006.01)

(52) U.S. Cl.
CPC .............. *A61N 5/103* (2013.01); *A61N 5/1031* (2013.01); *A61N 5/1071* (2013.01)

(58) Field of Classification Search
USPC ........................................................... 378/65
See application file for complete search history.

(56) References Cited

U.S. PATENT DOCUMENTS

| | | | |
|---|---|---|---|
| 7,945,022 B2 | 5/2011 | Nelms et al. | |
| 2004/0165696 A1* | 8/2004 | Lee | A61N 5/1031 378/65 |
| 2012/0041685 A1* | 2/2012 | Ding | A61B 6/032 702/19 |
| 2012/0305793 A1* | 12/2012 | Schiefer | A61N 5/1048 250/394 |
| 2013/0193351 A1* | 8/2013 | Cheng | A61N 5/1037 250/492.1 |

OTHER PUBLICATIONS

Low; et al, "A technique for the quantitative evaluation of dose distributions", Medical Physics, vol. 25, No. 5, May 1998, pp. 656-661.*
Wendling Markus et al: "A fast algorithm for gamma evaluation in 3D," Medical Physics, AIP, Melville, NY, US, vol. 34, No. 5, Apr. 19, 2007, pp. 1647-1654, XP012103402, Section II. Materials and Methods.
Yuan Jiankui et al: "A γ dose distribution evaluation technique using the k-d tree for nearest neighbor searching," Medical Physics, AIP, Melville, NY, US, vol. 37, No. 9, Aug. 20, 2010, pp. 4868-4873, XP0121449959, Section II. Methods and Materials.
Ann Van Esch et al: "The use of an aSi-based EPID for routine absolute dosimetric pre-treatment verification of dynamic IMRT fields," Radiotherapy and Oncology, vol. 71, No. 2, May 2004, pp. 223-234, XP055087412, Section 2.1. The aSi-based EPID for dosimetry in dynamic mode.
International Search Report and Written Opinion for International Application No. PCT/EP2013/070797, dated Nov. 19, 2013.
Wouter J.C. Van Elmpt et al., "A Monte Carlo based three-dimensional dose reconstruction method derived from portal dose images," Med. Phys. vol. 33, No. 7, Jul. 2006, pp. 2426-2434.
Cedric X. Yu, "Intensity Modulated Arc Therapy: Technology and Clinical Implementation," University of Maryland School of Medicine, Jun. 30, 2014 (downloaded).

(Continued)

*Primary Examiner* — Phillip A Johnston
(74) *Attorney, Agent, or Firm* — Shapiro, Gabor and Rosenberger, PLLC (57) ABSTRACT

Systems, devices, and methods for quality assurance for verification of radiation dose delivery in arc-based radiation therapy devices using a 3D gamma evaluation method.

31 Claims, 3 Drawing Sheets

(56) References Cited

OTHER PUBLICATIONS

Dayananda Shamurailatpam Sharma et al., "Portal dosimetry for pretreatment verification of IMRT plan: a comparison with 2D ion chamber array," Journal of Applied Clinical Medical Physics, vol. 11, No. 4, Fall 2010, pp. 238-248.

Simon R. Arridge et al., "Optical tomography: forward and inverse problems," arXiv:0907.2586v1 [math.AP] Jul. 15, 2009.

Kui Ren, "Recent Developments in Numerical Techniques for Transport-Based Medical Imaging Methods," Commun. Comput. Phys., vol. 8, No. 1, pp. 1-50, Jul. 2010.

Savino Cilla et al., "Comparison of measured and computed portal dose for IMRT treatment," Journal of Applied Clinical Medical Physics, vol. 7, No. 3, Summer 2006, pp. 65-79.

Daniel W. Bailey et al., "EPID dosimetry for pretreatment quality assurance with two commercial systems," Journal of Applied Clinical Medical Physics, vol. 13, No. 4, 2012, pp. 82-99.

Daniel A. Low et al., "A technique for the quantitative evaluation of dose distributions," Med. Phys. vol. 25, No. 5, May 1998, pp. 656-661.

Grace Tang et al., "Comparing Radiation Treatments Using Intensity-Modulated Beams, Multiple Arcs and Single Arc," Int J Radiat Oncol Bio Phys, Apr. 2010, 76(5), 1554-1562.

J. Godart et al., "Reconstruction of high-resolution 3D dose from matrix measurements: error detection capability of the COMPASS correction kernel method," Phys. Med. Biol. vol. 56 (2011), pp. 5029-5043.

Arthur J. Olch, "Evaluation of the accuracy of 3DVH software estimates of dose to virtual ion chamber and film in composite IMRT QA," Journal of Applied Clinical Medical Physics, vol. 11, No. 4, Fall 2010, pp. 81-86.

Steve Webb, "Volumetric-modulated arc therapy: its role in radiation therapy," Medical Physics Web, Jun. 25, 2009.

Chao Wang et al., "Arc-modulated radiation therapy (AMRT): a single-arc form of intensity-modulated arc therapy," Phys. Med. Biol. vol. 53 (2008), pp. 6291-6303.

Karin W. Lamberts et al., "Qualitative determination of errors causing portal dose differences using gamma evaluation parameters," Medical Engineering Technische Universiteit Eindhoven, Aug. 2005, Course Code: 8Z150.

Wouter Van Elmpt et al., "A literature review of electronic portal imaging for radiotherapy dosimetry," Radiotherapy and Oncology, vol. 88 (1008), pp. 289-309.

Sandra Correia Vieira, "Dosimetric Verification of Intensity Modulated Radiotherapy with an Electronic Portal Imaging Device," Department of Radiation Oncology, Division of Medical Physics, Erasmus MC/Daniel den Hoed Cancer Center, Groene Hilledijk 301, 3075 EA Rotterdam, The Netherlands, Jun. 30, 2014 (downloaded).

International Preliminary Report on Patentability issued Apr. 14, 2015, in International Application No. PCT/EP2013/070797.

* cited by examiner

SYSTEMS, DEVICES, AND METHODS FOR QUALITY ASSURANCE OF RADIATION THERAPY

FIELD

The present disclosure relates generally to delivering radiation to a patient, and more particularly to systems, methods, and computer program products for performing quality control measurements prior to and during radiation treatment.

BACKGROUND

Radiosurgery and radiotherapy systems are radiation therapy treatment systems that use external radiation beams to treat pathological anatomies (tumors, lesions, vascular malformations, nerve disorders, etc.) by delivering prescribed doses of radiation (X-rays, gamma rays, electrons, protons, and/or ions) to the pathological anatomy while minimizing radiation exposure to the surrounding tissue and critical anatomical structures. Radiotherapy is characterized by a low radiation dose per fraction (e.g., 100-200 centiGray), shorter fraction times (e.g., 10-30 minutes per treatment), and hyper fractionation (e.g., 30-45 fractions), and repeated treatments. Radiosurgery is characterized by a relatively high radiation dose per fraction (e.g., 500-2000 centiGray), extended treatment times per fraction (e.g., 30-60 minutes per treatment), and hypo-fractionation (e.g. 1-5 fractions or treatment days). Due to the high radiation dose delivered to the patient during radiosurgery, radiosurgery requires high spatial accuracy to ensure that the tumor or abnormality (i.e., the target) receives the prescribed dose while the surrounding normal tissue is spared.

In general, radiosurgery and radiotherapy treatments consist of several phases. First, a precise three-dimensional (3D) map of the anatomical structures in the area of interest (head, body, etc.) is constructed using any one of a computed tomography (CT), cone-beam CBCT, magnetic resonance imaging (MRI), positron emission tomography (PET), 3D rotational angiography (3DRA), or ultrasound techniques. This determines the exact coordinates of the target within the anatomical structure, namely, locates the tumor or abnormality within the body and defines its exact shape and size. Second, a motion path for the radiation beam is computed to deliver a dose distribution that the surgeon finds acceptable, taking into account a variety of medical constraints. During this phase, a team of specialists develop a treatment plan using special computer software to optimally irradiate the tumor and minimize dose to the surrounding normal tissue by designing beams of radiation to converge on the target area from different angles and planes. Third, the radiation treatment plan is executed. During this phase, the radiation dose is delivered to the patient according to the prescribed treatment plan.

There are many factors that can contribute to differences between the prescribed radiation dose distribution and the actual dose delivered (i.e., the actual dose delivered to the target during the radiation treatment). One such factor is uncertainty in the patient's position in the radiation therapy system. Other factors involve uncertainty that is introduced by changes that can occur during the course of the patient's treatment. Such changes can include random errors, such as small differences in a patient's setup position. Other sources are attributable to physiological changes that might occur if a patient's tumor regresses or if the patient loses weight during therapy. Another category of uncertainty includes motion. Motion can potentially overlap with either of the categories as some motion might be more random and unpredictable, whereas other motion can be more regular. These uncertainties can affect the quality of a patient's treatment and the actual radiation dose delivered to the target.

The accuracy in delivering a predicted radiation dose to a target based on a predetermined treatment plan, therefore, plays an important role in the ultimate success or failure of the radiation treatment. Inaccurate dose delivery can result in either insufficient radiation for cure, or excessive radiation to nearby healthy tissue. Quality assurance tools and protocols are therefore needed to verify that the prescribed radiation dose is delivered to the target.

In radiation therapies, radiation delivery is made based on the assumption that the radiation treatment plan was developed based on correct information, the position of the radiation beam relative to the patient set-up is correctly calibrated, and that the radiation therapy system not only functions properly but that it also functions based on correct and consistent external inputs used to program the system. However, if the calibration of the support device, for example, is incorrect, or the system functions improperly, or the treatment plan includes incorrect information, an incorrect dose will be delivered to the target during treatment even if the radiation therapy system operates as instructed. A radiation dose that is too high may cause serious damage to healthy tissues surrounding the tumor, whereas a dose that is too low may jeopardize the probability of cure. Therefore, a relatively small error in the delivered radiation dose may seriously harm the patient.

SUMMARY

The present disclosure includes systems, methods, devices, and computer program products for radiation treatment quality assurance protocol implementation.

The present disclosure also includes systems, methods, devices, and computer program products for pre-treatment and treatment dosimetry verification.

The present disclosure also provides systems, methods, and computer program products for dosimetric verification of treatment techniques.

The present disclosure also provides systems, methods, and computer program products for pretreatment dose verification.

The present disclosure also provides systems, methods, and computer program products for in-vivo dose verification.

The present disclosure also provides systems, methods, and computer program products for dosimetric verification during arc therapy treatment using a portal dose imaging device.

The present disclosure also provides systems, methods, and computer program products for quantitative evaluation of dose distributions.

The present disclosure also provides systems, methods, and computer program products for evaluating dose distributions using a 3D gamma function.

The present disclosure also provides systems, methods, and computer program products for evaluating dose distributions using a 3D gamma function.

The present disclosure also provides methods for verifying quantities of interest of a radiation beam in an arc-based radiation therapy device including a gantry, comprising: generating radiation dose distribution images at predetermined radiation fields, each radiation field corresponding to a predetermined arc segment of the gantry; and comparing the generated radiation dose distribution images with corresponding predicted radiation dose distribution images using a three-dimensional (3D) gamma evaluation method including dose differences, spatial differences, and angular differences between points in the generated images and corresponding points in the predicted images as parameters.

The method can further comprise storing all generated radiation dose distribution images as a first data set mapped as a first 3D array including 3D positional information of the points in the generated images, wherein the 3D positional information includes spatial and angular locations of the delivered beams (X, Y, θ).

The method can further comprise storing all predicted radiation dose distribution images as a second data set mapped as a second 3D array including 3D position information of the points in the predicted images, wherein the 3D positional information includes spatial and angular locations of the predicted beams (X, Y, θ).

The method can further comprise comparing the first and second data sets using the 3D gamma evaluation method.

The present disclosure also provides a system for verifying quantities of interest of a radiation beam in an arc-based radiation therapy device including a gantry, comprising: a portal dose imaging device adapted to measure incident radiation dose from each predetermined radiation field, each radiation field corresponding to a predetermined arc segment of the gantry, the portal dose imaging device being further configured to generate two-dimensional (2D) portal images for each arc segment; and a processing device operably connected to the portal dose imaging device and being configured to convert the 2D portal images to 2D portal dose images and to store the plurality of measured 2D portal dose images in a first 3D array having spatial and angular locations of the delivered beams (X, Y, θ) as dimensions, the processing device being further configured to store a plurality of predicted 2D portal dose images in a second 3D array having spatial and angular locations of the predicted beams (X, Y, θ) as dimensions.

The processing device can be further configured to compare points in the first 3D array with corresponding points in the second 3D array using a 3D gamma evaluation method, the gamma evaluation method including dose differences, spatial differences, and angular differences between corresponding points in the first and second 3D arrays as parameters.

The errors in the quantities of interest can be determined based on the comparison.

The present disclosure also provides a non-transitory computer-readable storage medium upon which is embodied a sequence of programmed instructions for quality control in a radiation therapy treatment system as disclosed herein, including a computer processing system, as disclosed herein, which executes the sequence of programmed instructions embodied on the computer-readable storage medium to cause the computer processing system to perform the steps of the method as disclosed herein.

BRIEF DESCRIPTION OF THE DRAWINGS

The drawings described herein are for illustration purposes only and are not intended to limit the scope of the present disclosure in any way. The invention will be best understood by reading the ensuing specification in conjunction with the drawing figures, in which like elements are designated by like reference numerals. As used herein, various embodiments can mean some or all embodiments.

DETAILED DESCRIPTION

To verify that a radiation treatment procedure is correctly applied, quality assurance protocols for verification of patient set-up, visualization of organ motion, dosimetric verification of the treatment plan, as well as in-vivo dosimetry can be implemented at corresponding stages of the radiation therapy. Quality assurance protocols are implemented to verify that the developed treatment plan is accurate, the treatment delivery is accurate, and that the actual dose delivered to the patient is the planed dose.

Quality assurance is especially needed in advanced radiotherapy techniques, such as, intensity-modulated radiotherapy (IMRT) or arc therapy, where in order to concentrate the dose inside the tumor while sparing the organs at risk, the treatment plan often has a high gradient dose distribution. Thus, quality control procedures in IMRT are needed for treatment planning, patient set-up, and beam delivery, i.e., pretreatment verification, as well as for a treatment or in-vivo verification. Treatment execution verification in IMRT generally includes two steps. A first step involves pre-treatment measurements and a second step involves during treatment measurements. The pre-treatment measurements are performed to check the proper transfer of treatment parameters from the planning phase to the specific IMRT device prior to the first treatment of the patient. It also ensures that the execution of the treatment plan by the device is correct. This includes verification that the correct fluence profiles are delivered. Pre-treatment verification is thus a procedure comparing the whole or at least part of the intended treatment plan with measurements of corresponding radiation beams delivered by a linear accelerator outside the patient treatment time, namely, with open fields or a phantom. This comparison focuses on predicted and measured leaf positions, dose delivered to the detector or phantom, or incident energy fluence extracted for measurements.

The during (or "in") treatment verification is a procedure that focuses on comparing of all or part of the planned and the delivered dose distribution based on measurements acquired during treatment of the patient. These measurements can then be used to determine the dose delivered to the detector or patient, or incident energy fluence obtained from measurements.

The dosimetry methods for verification of both the pre-treatment and treatment verification can include: non-transmission dosimetry, which includes a determination of the dose in the detector, patient, or phantom, or a determination of the incident energy fluence, based on measurements without an attenuating medium between the source of radiation and the detector (i.e., phantom or patient); transmission dosimetry, which includes a determination of the dose at the position of the detector, patient or phantom, or determination of the incident energy fluence, based on radiation transmitted through the patient or phantom; in-phantom dosimetry, which includes a determination of the dose inside the phantom (the dose could be at points, lines, planes, or volumes within the phantom); and in-vivo dosimetry, which includes measurement or determination of the dose inside the patient (this can be performed invasively, i.e., inside the patient, or non-invasively, i.e., on or some distance from the patient, whereby the in-vivo dose at the point of interest is obtained by extrapolation).

Dose verification in arc therapy can be performed at different locations with different configurations of the dosimeter. When an electronic portal dose imager (EPID) is used as the dosimeter, the following dose verification options are available:

(a) non-transmission pre-treatment dosimetry: acquiring an image for each field without patient or phantom in the beam and:
   comparing acquired image (raw image or converted to dose distribution image) with predicted EPID response or predicted dose image (PDI) at the level of the imager (portal dosimetry); or
   comparing dose reconstructed inside the patient/phantom CT scan (convert image to energy fluence, use as input for dose calculation algorithm) with plan calculated with patient/phantom CT scan.

(b) non-transmission treatment dosimetry: acquiring image for each field with the detector located between source and patient during treatment and:
   comparing acquired image (raw image or converted to dose distribution image) with predicted EPID response or predicted dose image (PDI) at the level of the imager during treatment time (portal dosimetry); or
   comparing dose reconstructed inside the patient/phantom CT scan (convert treatment image to energy fluence, use as input for dose calculation algorithm) with plan calculated with patient/phantom CT scan.

(c) transmission treatment dosimetry: acquiring image for each field with the detector located behind the patient or phantom and:
   comparing acquired image (raw image or converted to dose distribution image) with predicted EPID response or predicted dose image (PDI) at the level of the imager, behind the patient/phantom (portal dosimetry); or
   comparing reconstructed dose inside the patient CT scan either back-project primary signal (using correction based algorithms) or convert image to energy fluence, use as input for dose calculation algorithm with plan calculated with patient CT scan.

Quality assurance of an arc field using portal dosimetry generally includes dividing the arc field into arc segments (roughly 10 segments, for example) for evaluation. The radiation at each segment of the arc field is measured with a portal dose imaging device, such as an electronic portal dose imager (EPDI), for example. The portal dose imager accumulates the signals from a segment and produces a 2D image. This image is then compared to an image predicted by a portal dose distribution algorithm. The images are individually compared. The comparison model generally used for comparing the measured and the predicted images is a 2D gamma or an L2 function. Such comparison models, however, suffer from reduced angular resolutions and are laborious. The (3D) gamma portal dose distribution comparison model disclosed herein solves the angular resolution problem of the prior art methods.

Figure 1A:
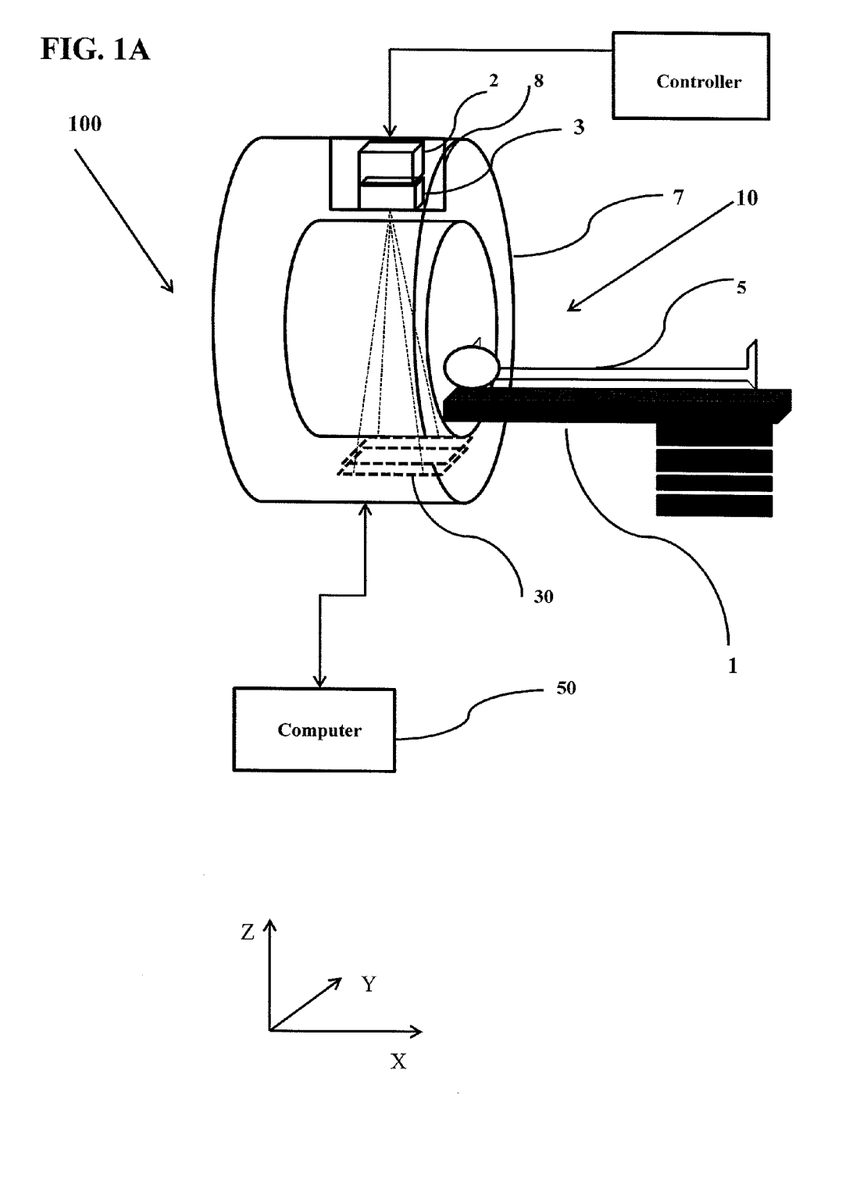
FIGS. 1A and 1B are perspective views of a radiation therapy system according to an embodiment of the invention.
Figure 1B:
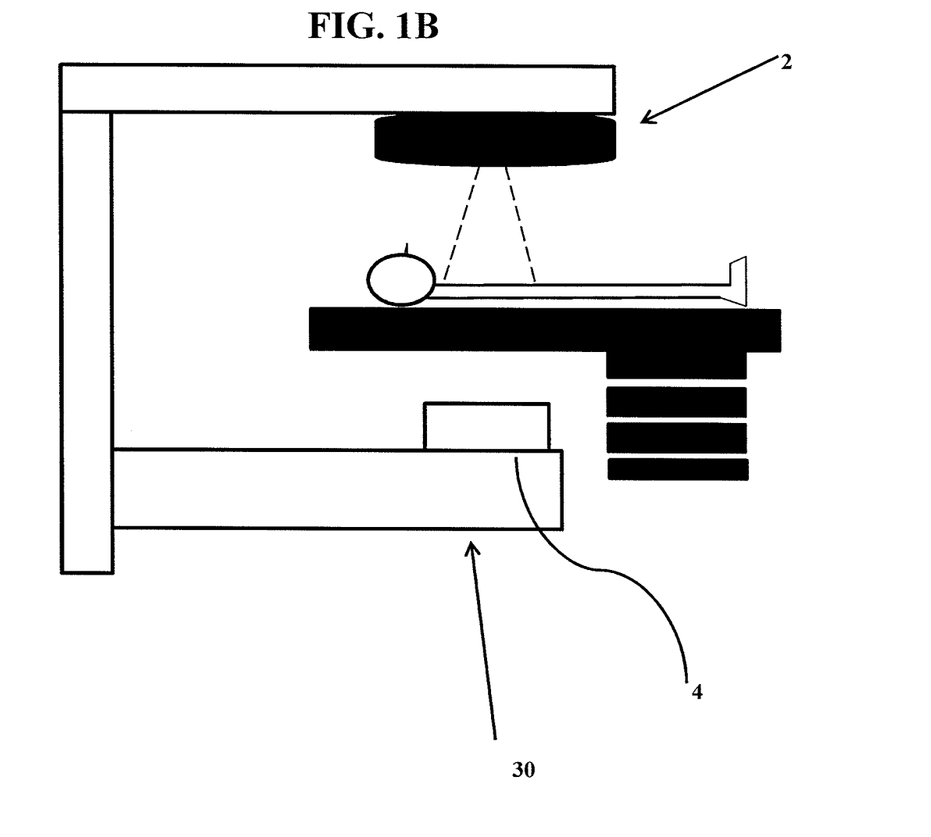

FIGS. 1A and 1B illustrate an exemplary radiation therapy treatment system 100 that can provide radiation therapy to a patient 5 and allows for various pre-treatment and treatment portal dosimetry verification. The radiation therapy treatment can include photon-based radiation therapy, particle therapy, electron beam therapy, or any other type of treatment therapy. In an embodiment, the radiation therapy treatment system 100 includes a radiation treatment device 10, such as, but not limited to, a radiotherapy or radiosurgery device, which can include a gantry 7 supporting a radiation module 8 which includes one or more radiation sources 3 and a linear accelerator 2 operable to generate a beam of kV or MV X-ray radiation. The gantry 7 can be a ring gantry (i.e., it extends through a full 360 degree arc to create a complete ring or circle), but other types of mounting arrangements may also be employed. For example, a C-type, partial ring gantry, or robotic arm could be used. Any other framework capable of positioning the radiation module 8 at various rotational and/or axial positions relative to the patient 5 may also be used. The radiation module 8 can also include a modulation device (not shown) operable to modulate the radiation beam as well as to direct a therapeutic radiation beam toward the patient 5 and toward a portion of the patient which is desired to be irradiated. The portion desired to be irradiated is referred to as the target or target region or a region of interest. The patient 5 may have one or more regions of interest that need to be irradiated. A collimation device (not shown) may be included in the modulation device to define and adjust the size of an aperture through which the radiation beam may pass from the source 3 toward the patient 5. The collimation device may be controlled by an actuator (not shown) which can be controlled by a computer processing system 50 and/or a controller 40.

In an embodiment, the radiation therapy device is a kV or MV energy intensity modulated radiotherapy (IMRT) device. The intensity profiles in such a system are tailored to the treatment requirements of the individual patient. The intensity modulated radiotherapy fields are delivered with a multileaf collimator (MLC), which is a computer-controlled mechanical beam shaping device attached to the head of the linear accelerator and includes an assembly of metal fingers or leaves. The MLC can be made of 120 movable leaves with 0.5 and/or 1.0 cm diameter, for example. For each beam direction the optimized intensity profile is realized by sequential delivery of various subfields with optimized shapes and weights. From one subfield to the next, the leaves may move with the radiation beam on (i.e., dynamic multileaf collimation (DMLC)) or with the radiation beam off (i.e., segmented multileaf collimation (SMLC). The device 10 can also be a tomotherapy device where intensity modulation is achieved with a binary collimator which opens and closes under computer control. As the gantry continuously rotates around the patient, the exposure time of a small width of the beam can be adjusted with the opening and closing of the binary collimator, allowing the radiation to be delivered to the tumor through the most preferred directions and locations of the patient. The device 10 can also be a helical tomotherapy device which includes a slip-ring rotating gantry. The device 10 can also be an intensity modulated arc therapy device (IMAT) where instead of using rotating fan beams, rotational cone beams of varying shapes are used to achieve intensity modulation. The device 10 can also be a simplified intensity modulated arc therapy (SIMAT) device which uses multiple arcs, or a sweeping window arc therapy device (SWAT), where the MLC leaf positions sweep across the PTV with rotation. In summary, any type of intensity modulated radiotherapy (IMRT) device can be used. In another embodiment, the device 10 is a self-shielded radiosurgery device, such as but not limited to, an arc-type X-ray image guided self-shielded radiosurgery device. Such a set-up enables the radiation sensor(s) 4 to be positioned directly opposite the therapeutic radiation source(s) 3 because it can be positioned outside specialized radiation bunkers. This setup makes it possible to continuously detect the therapeutic beam energy after it passes through the target volume. Each type of device 10 is accompanied by a corresponding radiation plan and radiation delivery procedure.

The device 10 further includes a portal dose imaging device 30 for acquiring digital images to be used for portal dosimetry verification. The portal dose imaging device 30 can be an electronic portal dose imaging device (EPID). The EPID 30 can be placed at different locations, such as, on top of the treatment couch 1, or attached to the accelerator head 2, etc., depending on whether non-transmission pre-treatment, or non-transmission treatment, or transmission treatment dosimetry is used for the quality assurance protocol. The portal dose imaging device 30 can generate immediate 2D digital information. It can be a camera-based device, such as a CCD camera-based EPID or an amorphous silicon based detector. The EPID 30 can also be a CCD-camera based EPID, which is effectively an array of 1280×1240 simultaneously integrating dosimeters with a dead time in between acquired frames of about 0.1 ms, for example. Another alternative is a flat panel imager (or amorphous silicon EPID), which also offers good image quality, high optical transfer efficiency, large imaging area, and resistance to radiation. The flat panel imager generally consists of picture elements (pixels) that register the amount of radiation that falls on them and convert the received amount of radiation into a corresponding number of electrons. The electrons are converted into electrical signals which are further processed using either the imaging device 30 or a computer 50. Such a configuration (i.e., digital imaging detector(s) positioned opposite the therapeutic source(s)) provides the ability to capture immediately the energy and intensity of the therapeutic radiation transmitted from each arc field segment and through the target volume (when used in-vivo) in order to generate two-dimensional (2D) images of digitized X-ray measurements. Because the portal dose imaging device 30 generates immediate, 2D digital information, it facilitates 2D dosimetry at any gantry angle.

As part of the quality control protocol, for pre-treatment portal dosimetry verification of arc fields, the radiation dose distribution delivered by the IMRT treatment fields is validated before starting the patient treatment. As such, before the first treatment fraction, 2D portal images (EPIs) are acquired using the electronic portal dose imaging device (EPID) 30 for each arc field segment in the absence of the patient. Each portal image (EPI) is measured under the same condition as the actual treatment but without the patient placed in the beam. For each treatment beam, an EPID image is acquired during full IMRT delivery with the radiation beams at the planned gantry angles θ. The EPID 30 receives data from different projection angles $0 \leq \theta \leq 360°$ as the linear accelerator 2 rotates around the gantry 7. The EPID 30 collects the transmitted radiation from each segment. The various segments for a single beam are integrated and a single 2D digital image per beam (i.e., per gantry angle) is generated. The raw 2D images are sent to the computer 50 for further processing.

The computer 50 includes typical hardware such as a processor, and an operating system for running various software programs and/or communication applications. The computer can include software programs that operate to communicate with the radiation therapy device 10, and the software programs are also operable to receive data from any external software programs and hardware. The computer 50 can also include any suitable input/output devices adapted to be accessed by medical personnel, as well as I/O interfaces, storage devices, memory, keyboard, mouse, monitor, printers, scanner, etc. The computer 50 can also be networked with other computers and radiation therapy systems. Both the radiation therapy device 10 and the computer 50 can communicate with a network as well as a database and servers. The computer 50 is also adapted to transfer medical image related data between different pieces of medical equipment.

The system 100 can also include a plurality of modules containing programmed instructions which communicate with each other and cause the system 100 to perform different functions related to radiation therapy/surgery, as discussed herein, when executed. For example, the system 100 can include a treatment plan module operable to generate the treatment plan for the patient 5 based on a plurality of data input to the system by the medical personnel, the treatment plan including a predicted radiation dose distribution, a patient positioning module operable to position and align the patient 5 with respect to the isocenter of the gantry 7 for a particular radiation therapy treatment, an image acquiring module operable to instruct the radiation therapy device 10 to acquire images of the patient 5 prior to the radiation therapy treatment and/or during the radiation therapy treatment (i.e., in-vivo images), and/or to instruct other imaging devices or systems to acquire images of the patient 5.

The system 100 can further include a treatment delivery module operable to instruct the radiation therapy device 10 to deliver the treatment plan to the patient 5, a converting module operable to convert the 2D portal images (EPIs) into 2D portal dose images (PDIs), an analysis module operable to compute comparisons between predicted and measured dose distributions, and a calculation module operable to calculate dose delivery errors. The analysis module can further include computational algorithms to quantitatively compare the measured and the predicted dose distributions. The modules can be written in the C or C++ programming languages, for example. Computer program code for carrying out operations of the invention as described herein may also be written in other programming languages.

The raw 2D images obtained at all arc field segments (i.e., measured EPIs) can be converted into corresponding 2D portal dose images (PDIs) using a portal dose reconstruction model. Portal dose distribution images (PDIs) represent absolute dose distributions at the plane of the EPID, and are obtained by converting gray scale pixel values to dose values or simulation of the gray scale pixel values. To convert portal images to portal dose images, any one of an empirical or simulation models can be used. In the first model, the EPID signal is converted to dose using a calibrated detector, such as, but not limited to, an ionization chamber inside water, or a mini-phantom, or film. The second approach simulates or models the detector response by Monte Carlo or other empirical simulation techniques.

The obtained 2D PIDs are stored in the computer processor 50 in a three-dimensional (3D) container having the X and Y positions of the imaging panel (EPID) as well as the corresponding gantry angles 8, as the 3D container dimensions. A container in general is a class, a data structure, or an abstract data type whose instances are collections of other objects. Containers are used for storing objects in an organized way following specific access rules. The size of the container depends on the number of the objects it contains. Since the plurality of measured 2D PIDs represents a series of image point locations/positions at different gantry angles θ, the plurality of 2D PDIs can be stored as a data set mapped as a 3D array having 3D position information of the image points. The predicted 2D dose images (predicted IPDs) can also be stored in a 3D container similar to the one used for storing the plurality of measured IPDs. Predicted 2D IPDs are images that were either previously generated for the treatment plan or generated independently of the treatment plan from planned treatment parameters using portal dose prediction models, such as, but not limited to, pencil beam prediction models, Monte Carlo simulation models, etc.

Using predetermined access rules, elements of the first 3D container (which stores measured image data) can be compared with corresponding elements of the second 3D container (which stores predicted image data), using a 3D gamma evaluation method as described in detail herein. Using this 3D gamma function, a robust comparison can be made between the measured IPDs and the corresponding predicted IPDs. Differences between the measured and predicted dose images are indications of radiation dose delivery errors. Dose delivery errors can signal erroneous treatment parameters, machine output variation, and/or changes in patient set-up and patient shape including organ motion.

Gamma evaluation is a method generally used to quantitatively compare dose distributions. The gamma method uses a comparison between a measured and predicted dose distribution. The gamma evaluation method combines a dose difference criterion with a distance-to-agreement (DTA) criterion which makes it a suitable method for both low and high dose gradient regions. Dose distributions can be subdivided into regions of low and high dose gradients, each with a different acceptance criterion. High dose gradients could be regions defined as pixels with maximum relative dose differences above 10% for neighboring pixels. In high dose gradient regions a small spatial error either in the calculation or the measurement results in a large dose difference between measurement and calculation. Dose difference in high dose gradient regions may therefore be unimportant, and the concept of distance-to-agreement (DTA) distribution is used to determine the acceptability of the dose calculation. The distance-to agreement DTA is the distance between a measured data point and the nearest point in the predicted dose distribution that exhibits the same dose. In high gradient regions, gamma evaluation parameters $\Delta x$ and $\Delta y$ are used to determine displacement, where $\Delta x$ and $\Delta y$ are the spatial distances between the measured and the predicted dose points in horizontal and vertical directions, respectively.

In low gradient regions, the doses are compared directly with an acceptance tolerance placed on the difference between the measured and calculated doses. A pixel is selected as low dose gradient if the maximum relative dose difference is below about 5% for all neighboring pixels. To determine dose variations, the relative dose difference between two PDIs is calculated by comparing each point in the measured dose distribution with the same point in the predicted dose distribution. A dose-difference distribution can be displayed that identifies the regions where the predicted dose distributions disagree with the measurement.

The gamma evaluation method is a technique that unifies dose distribution comparisons using acceptance criteria. The measure of acceptability is the multidimensional distance between the measurement and predicted points in both the dose and the physical distance. The gamma value or distance metric $\Gamma$ is a numerical quality index that serves as a measure of disagreement in the regions that fail the acceptance criteria and indicates the calculation quality in regions that pass. The passing criteria for dose difference criterion ($\Delta D_M$) and the DTA criterion ($\Delta d_M$) is generally 3% and 3 mm, respectively. The gamma value $\Gamma$ is calculated and compared with these criteria.

A general representation of the method for determining an acceptance criteria that considers both the dose difference and the DTA is as follows:

$$\Gamma(r_p, r_m) = \sqrt{\frac{r^2(r_p, r_m)}{\Delta d^2} + \frac{\delta^2(r_p, r_m)}{\Delta D^2}} \quad (1)$$

where $r(r_p, r_m) = \sqrt{\Delta x_{p-m}^2 + \Delta y_{p-m}^2}$ and (2)

$\delta(r_p, r_m) = D_p(r_p) - D_m(r_m)$ (3)

with r being the spatial distance between a predicted point $r_p$ in the predicted portal dose distribution and a corresponding measured point $r_m$ in the measured dose distribution; X and Y represent the spatial locations of the predicted and measured points $r_p$ and $r_m$ along the X and Y axis (i.e., horizontal and vertical directions), with $x_p$ and $x_m$ indicating the locations along the X axis of the predicted and measured points point $r_p$ and $r_m$, respectively, and $y_p$ and $y_m$ indicating the locations along the Y axis of the predicted and measured points $r_p$ and $r_m$, respectively; $\delta$ indicating the dosimetric difference, namely, the difference between the dose values on the predicted and measured distributions, with $D_p$ representing the predicted dose value and $D_m$ the measured dose value. The gamma value $\Gamma$ is calculated for a specific predicted point in the measured image. The same predicted point is compared to other points in the measured image. For all points, a gamma value $\Gamma$ is computed and the minimum of these values is the gamma index or gamma error value $\gamma$ which belongs to the predicted point $r_p$:

$$\gamma(r_p) = \min\{\Gamma(r_m, r_p)\} \forall \{r_m\} \quad (4)$$

meaning that the gamma value is the minimum generalized gamma value $\Gamma$ in the set of evaluated values. This calculation is done for all points in the predicted image. The gamma function $\gamma$ is thus determined. The pass-fail criteria is then determined by the following:

$$\gamma(r_p) \leq 1, \text{calculation passes} \quad (5)$$

$$\gamma(r_p) > 1, \text{calculation fails} \quad (6)$$

In order to robustly compare the stored measured and the predicted PDIs s, Equation1 is expanded to take into consideration the gantry angle $\theta$ as another dimension. Equation 1 then becomes:

$$\Gamma(r_p, r_m, \theta) = \sqrt{s_{xy} r^2(r_p, r_m) + s_d \delta^2(r_p, r_m) + s_\theta \Delta\theta^2(\theta_p, \theta_m)} \quad (7)$$

which, when combined with Equations 2 and 3, gives the gamma value $\Gamma$:

$$\Gamma(r_p, r_m, \theta) = \quad (8)$$
$$\sqrt{s_{xy}(\Delta x_{p-m}^2 + \Delta y_{p-m}^2) + s_d(D_p(r_p, \theta_p) - D_m(r_m, \theta_m))^2 + s_\theta \Delta\theta^2(\theta_p, \theta_m)}$$

as the distance to closest point in the predicted volume.
The angular distance between the predicted and the measured points $r_p$ and $r_m$ is:

$$\Delta\theta = \theta_p - \theta_m \quad (9),$$

and the dosimetric difference between the predicted and measured value at gantry angle $\theta$ is: $\Delta D = D_p(x_p, y_p, \theta_p) - D_m(x_m, y_m, \theta_m)$ (10)

When the measured dose distribution image (i.e. image 1) is compared to the predicted dose distribution image (i.e., image 2), the gamma value becomes:

$$\Gamma((x_1, y_1, \theta_1), (x_2, y_2, \theta_2)) = \sqrt{s_{xy}(\Delta x^2 + \Delta y^2) + s_d(\Delta D)^2 + s_\theta \Delta\theta^2} \quad (11)$$

with:

$$\Delta D = D_1(x_1, y_1, \theta_1) - D_2(x_2, y_2, \theta_2) \quad (12)$$

$$\Delta x = x_1 - x_2 \quad (13)$$

$$\Delta x = y_1 - y_2 \quad (14)$$

$$\Delta\theta = \theta_1 - \theta_2 \quad (15)$$

and $s_{xy}$, $s_d$, and $s_\theta$ being scalars of the respective dimensions, namely, $s_{xy}$ is the scalar for the horizontal and vertical positions X, Y, $s_d$ being the scalar for the predicted and measured dose, and $s_\theta$ being the scalar for the angular position. The dose, the XY position, and the gantry angle dimensions can be scaled independently.

The gamma error function then becomes:

$$\gamma(r_p) = \min\{\Gamma(r_m, r_p, \theta)\} \forall \{r_m\} \quad (16)$$

This 3D gamma function provides a 3D matrix of gamma errors with high angular resolution. The 3D error matrix can be further reduced to a 2D error matrix to simplify the evaluation. The reduced 2D error matrix could be, for example, the sum of the error planes over angular dimensions, or a point wise maximum over the angular dimensions. This 3D gamma function can thus provide a practical and reliable comparison model to robustly compare the measured dose distribution with a predicted dose distribution. The 3D gamma evaluation method described herein can also make a distinction between errors caused by dose differences and displacement of a patient or organ motion, because changes in the portal dose distribution caused by patient or organ displacement does not influence the sensitivity of the error qualification method in low dose gradient regions. This method therefore can be used for automated error detection using EPIDs.

In an alternative embodiment, instead of converting the measured 2D EPIs into PDIs, the raw EPI images can be used for storing into a 3D container and for comparison with the predicted PDIs.

For treatment verification, the portal dose imaging device 30 can be positioned such that the detector 4 and the therapeutic radiation source 3 are arranged to be directly opposite from each other, and so that the detector 4 can continuously receive during the treatment the therapeutic radiation beams that passed through the target region of the patient 5. The portal dose imaging device (EPID) 30 then allows for the detecting and recording the transmission of the therapeutic X-ray beams from the source 3 that passes through the patient 5. In this case, the treatment verification focuses on comparing of all or part of the planned and the delivered dose distribution based on measurements acquired during treatment of the patient. These measurements can then be used to determine the dose delivered to the detector or patient, or incident energy fluence obtained from measurements.

The difference between the pre-treatment and the treatment verification protocols is that during treatment verification, the 2D EPI images are acquired during radiation treatment of the patient 5. Otherwise, the conversion, storing, and 3D gamma comparison processes are the same as those for the pre-treatment verification, described herein.

Figure 2:
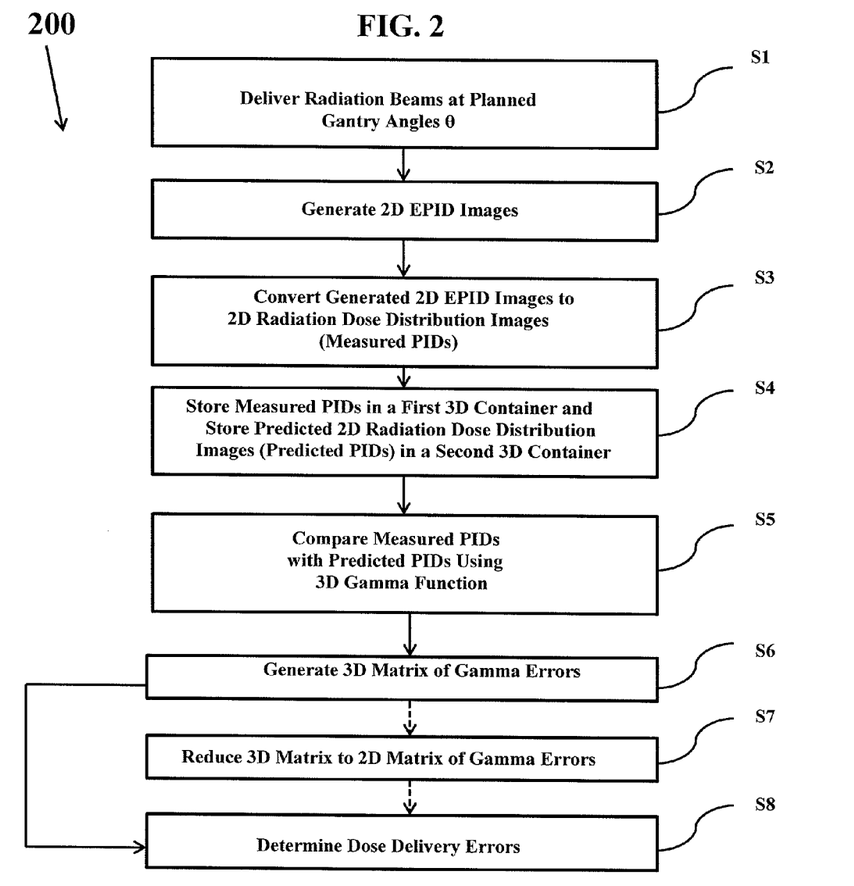
FIG. 2 is a flow chart of a quality control procedure according to various embodiments.

The quality control and verification process 200 is shown in FIG. 2. In Step 1 (S1), radiation beams are delivered at the planned clinical gantry angles. For each treatment beam delivered at a specific gantry angle, a corresponding 2D EPID image is acquired (S2). In Step 3 (S3), all of the measured 2D images are converted into 2D portal dose images (PDIs). In Step 4 (S4), the plurality of measured PDIs are stored in a first 3D container, and the plurality of predicted PDIs are stored in a second 3D container. In Step 5 (S5), the measured PDIs in the first 3D container are robustly compared to the corresponding predicted PDIs stored in the second 3D container using a (3D) gamma function which includes angular difference as an additional dimension. In Step 6 (S6), a 3D matrix of gamma errors is generated using the 3D gamma function. In optional Step 7 (S7), the 3D matrix error is reduced to a 2D error matrix. In Step 8 (S8) the radiation dose delivery errors are determined.

A non-transitory computer readable medium can be used to store the software or programmed instructions and data which when executed by a computer processing system 50 causes the system to perform various methods of the present invention, as discussed herein. The executable software and data may be stored in various places, including, for example, the memory and storage of the computer processing system 50 or any other device that is capable of storing software and/or data.

Accordingly, embodiments of quality control systems, methods and computer program products have been disclosed. Many alternatives, modifications, and variations are enabled by the present disclosure. Features of the disclosed embodiments can be combined, rearranged, omitted, etc. within the scope of the invention to produce additional embodiments.

Also, a non-transitory computer-readable storage medium is disclosed upon which is embodied a sequence of programmed instructions for quality control in a radiation therapy treatment system including a computer processing system which executes the sequence of programmed instructions embodied on the computer-readable storage medium to cause the computer processing system to perform the steps of: for each treatment beam, acquiring a 2D image; converting all 2D images acquired into portal dose images (measured PDIs); storing the plurality of measured PDIs as a data set mapped as a 3D array having 3D position information of the images; storing the plurality of predicted PDIs as a data set mapped as a 3D array having 3D position information of the predicted images; comparing the measured 3D portal dose distribution images and the predicted portal dose distribution images using a 3D gamma function which includes angular difference as a dimension; generating a 3D matrix of gamma errors using the 3D gamma function; reducing the 3D matrix error to a 2D error matrix; and calculating dose delivery errors based on the comparison.

Furthermore, certain features of the disclosed embodiments may sometime be used to advantage without a corresponding use of other features. Accordingly, Applicants intend to embrace all such alternatives, modifications, equivalents, and variations that are within the spirit and scope of the present disclosure.

While embodiments and applications of this invention have been shown and described, it would be apparent to those skilled in the art that many more modifications are possible without departing from the inventive concepts herein. The invention is not limited to the description of the embodiments contained herein, but rather is defined by the claims appended hereto and their equivalents.

What is claimed is:

1. A method for verifying quantities of interest of a radiation beam in an arc-based radiation therapy device including a gantry, comprising:
   acquiring and converting 2D images in order to
   generate radiation dose distribution images at predetermined radiation fields, each radiation field corresponding to a predetermined arc segment of the gantry;
   comparing the generated radiation dose distribution images with corresponding predicted radiation dose distribution images using a three-dimensional (3D) gamma evaluation method, the comparing including:
   calculating dose differences, spatial differences, and angular differences between points in the generated images and corresponding points in the predicted images; and
   evaluating the calculated differences using a gamma error function, the gamma error function determining minimums of a metric comprising the calculated dose, spatial, and angular differences for the points evaluated in the generated image; and determining acceptability of a quantity of interest based on a result of the evaluation.

2. The method of claim 1, further comprising storing the generated radiation dose distribution images in a data structure where positional information of the points in the generated images are stored together with corresponding values of the points.

3. The method of claim 2, wherein the storing includes storing the generated radiation dose distribution images as a first data set mapped as a first 3D data array including 3D positional information of the points in the generated images.

4. The method of claim 3, wherein the 3D positional information includes spatial and angular locations of the delivered beams (X, Y, θ).

5. The method of claim 3, further comprising storing the predicted radiation dose distribution images as a second data set mapped as a second 3D data array including 3D position information of the points in the predicted images.

6. The method of claim 5, wherein the 3D positional information includes spatial and angular locations of the predicted beams (X, Y, θ).

7. The method of claim 5, wherein the comparing includes comparing the first and second data sets using the 3D gamma evaluation method.

8. The method of claim 1, further comprising computing a 3D gamma error matrix based on the following gamma error function:

$$\gamma(r_p) = \min\{\Gamma(r_m, r_p, \theta)\} \forall \{r_m\},$$

wherein the gamma value γ in the 3D matrix is a minimum value of a distance metric Γ indicating a measure of acceptability of a quantity of interest.

9. The method of claim 8, further comprising calculating distance metric values for each point in the first data set using:

$$\Gamma((x_m, y_m, \theta_m), (x_p, y_p, \theta_p)) = \sqrt{s_{xy}(\Delta x^2 + \Delta y^2) + s_d(\Delta D)^2 + s_\theta \Delta \theta^2}$$

wherein ΔD is the dosimetric difference between measured and predicted dose values, $\Delta x = x_m - x_p$ and $\Delta x = y_m - y_p$ are axial differences between corresponding points in the first and second data sets; and $\Delta \theta = \theta_m - \theta_p$ are angular differences between corresponding points in the first and second data sets.

10. The method of claim 9, further comprising reducing the 3D gamma error matrix to a 2D gamma error matrix.

11. The method of claim 1, wherein quantities of interest include radiation dose.

12. The method of claim 11, further including determining dose delivery errors based on the comparison.

13. A system for verifying quantities of interest of a radiation beam in an arc-based radiation therapy device including a gantry, comprising:

a portal dose imaging device adapted to measure incident radiation dose from each predetermined radiation field, each radiation field corresponding to a predetermined arc segment of the gantry, the portal dose imaging device being further configured generate two-dimensional (2D) portal images for each arc segment; and a processing device operably connected to the portal dose imaging device and being configured to convert the 2D portal images to 2D portal dose images and to store a plurality of measured 2D portal dose image data in a first 3D data array including 3D position information of points in the measured 2D portal dose images, and having spatial and angular locations of the delivered beams (X, Y, θ) as dimensions, the processing device being further configured to store a plurality of predicted 2D portal dose image data in a second 3D data array including 3D position information of points in the predicted 2D portal dose images, and having spatial and angular locations of the predicted beams (X, Y, θ) as dimensions;

the processing device being further configured to compare the points in the first 3D data array with corresponding points in the second 3D data array using a 3D gamma evaluation method, the gamma evaluation method including calculating dose differences, spatial differences, and angular differences between corresponding points in the first and second 3D data arrays as parameters;

the processing device being further configured to evaluate the calculated differences using a gamma error function, the gamma error function determining minimums of a metric comprising the calculated dose, spatial, and angular differences for the points evaluated in the generated image, and to determine acceptability of a quantity of interest based on a result of the evaluation, wherein errors in the quantities of interest are determined based on the comparison.

14. The system of claim 13, wherein the arc-field radiation therapy device is an intensity modulated radiation therapy device.

15. The system of claim 14, wherein portal imaging device is an electronic portal imaging device (EPID).

16. The system of claim 15, wherein the processing device is further configured to generate a 3D gamma error matrix based on the following gamma error function:

$$\gamma(r_p) = \min\{\Gamma(r_m, r_p, \theta)\} \forall \{r_m\},$$

wherein each gamma value γ in the 3D matrix is a minimum value of a distance metric Γ indicating a measure of acceptability of the quantity of interest.

17. The system of claim 13, wherein the processing device is further configured to calculate distance metric values for each point in the first 3D data array using:

$$\Gamma((x_m, y_m, \theta_m), (x_p, y_p, \theta_p)) = \sqrt{s_{xy}(\Delta x^2 + \Delta y^2) + s_d(\Delta D)^2 + s_\theta \Delta \theta^2}$$

wherein ΔD is the dosimetric difference between measured and predicted dose values, $\Delta x = x_m - x_p$ and $\Delta x = y_m - y_p$ are spatial differences between corresponding points in the first and second 3D data arrays; and $\Delta \theta = \theta_m - \theta_p$ are angular differences between corresponding points in the first and second 3D data arrays.

18. The system of claim 17, wherein the processing device is further configured to reduce the 3D gamma error matrix to a 2D gamma error matrix.

19. A non-transitory computer-readable storage medium upon which is embodied a sequence of programmed instructions for verifying quantities of interest of a radiation beam in a system including an arc-based radiation therapy device including a gantry and a computer processing system which executes the sequence of programmed instructions embodied on the computer-readable storage medium to cause the computer processing system to perform the steps of:

acquiring and converting 2D images in order to generate radiation dose distribution images at predetermined radiation fields, each radiation field corresponding to a predetermined arc segment of the gantry; and comparing the generated radiation dose distribution images with corresponding predicted radiation dose distribution images using a three-dimensional (3D) gamma evaluation method including calculating dose differences, spatial differences, and angular differences between points in the generated images and corresponding points in the predicted images as parameters, wherein the comparing includes evaluating the calculated differences using a gamma error function, the gamma error function determining minimums of a metric comprising the calculated dose, spatial, and angular differences for the points evaluated in the generated image, and determining acceptability of a quantity of interest based on a result of the evaluation.

20. The non-transitory computer-readable medium of claim 19, further comprising storing the generated radiation dose distribution images in a data structure where positional information of the points in the generated images are stored together with corresponding values of the points.

21. The non-transitory computer-readable medium of claim 20, wherein the storing includes storing the generated radiation dose distribution images as a first data set mapped as a first 3D data array including 3D positional information of the points in the generated images.

22. The non-transitory computer-readable medium of claim 21, wherein the 3D positional information includes spatial and angular locations of the delivered beams $(X, Y, \theta)$.

23. The non-transitory computer-readable medium of claim 21, further comprising storing the predicted radiation dose distribution images as a second data set mapped as a second 3D data array including 3D position information of the points in the predicted images.

24. The non-transitory computer-readable medium of claim 23, wherein the 3D positional information includes spatial and angular locations of the predicted beams $(X, Y, \theta)$.

25. The non-transitory computer-readable medium of claim 19, wherein the comparing includes comparing the first and second data sets using the 3D gamma evaluation method.

26. The non-transitory computer-readable medium of claim 25, further comprising computing a 3D gamma error matrix based on the following gamma error function:

$$\gamma(r_p) = \min\{\Gamma(r_m, r_p, \theta)\} \forall \{r_m\}$$

wherein each gamma value $\gamma$ in the 3D matrix is a minimum value of a distance metric $\Gamma$ indicating a measure of acceptability of a quantity of interest.

27. The non-transitory computer-readable medium of claim 26, further comprising calculating distance metric values for each point in the first data set using:

$$\Gamma((x_m, y_m, \theta_m), (x_p, y_p, \theta_p)) = \frac{1}{\sqrt{s_{xy}(\Delta x^2 + \Delta y^2) + s_d(\Delta D)^2 + s_\theta \Delta \theta^2}}$$

wherein $\Delta D$ is the dosimetric difference between measured and predicted dose values, $\Delta x = x_m - x_p$ and $\Delta x = y_m - y_p$ are axial differences between corresponding points in the first and second data sets; $\Delta \theta = \theta_m - \theta_p$ and are angular differences between corresponding points in the first and second data sets.

28. The non-transitory computer-readable medium of claim 27, further comprising reducing the 3D gamma error matrix to a 2D gamma error matrix.

29. The non-transitory computer-readable medium of claim 19, wherein quantities of interest include radiation dose.

30. The non-transitory computer-readable medium of claim 29, further including determining dose delivery errors based on the comparison.

31. A method for verifying quantities of interest of a radiation beam in an arc-based radiation therapy device including a gantry, comprising:

delivering radiation at a plurality of radiation fields corresponding to a predetermined arc segment of the gantry;

measuring transmitted or absorbed radiation from each arc segment using an electronic portal dose imaging device;

generating 2D images based on the measured radiation;

converting the 2D images into corresponding 2D portal dose images (PDIs) using a portal dose reconstruction model; and comparing the obtained 2D portal dose images with corresponding predicted radiation dose images using a three-dimensional (3D) gamma evaluation method including calculating dose differences, spatial differences, and angular differences between points in the generated images and corresponding points in the predicted images as parameters;

evaluating the calculated differences using a gamma error function, the gamma error function determining minimums of a metric comprising the calculated dose, spatial, and angular differences for the points evaluated in the generated image; and determining acceptability of a quantity of interest based on a result of the evaluation.

* * * * *